US012247087B2

United States Patent
Liu et al.

(10) Patent No.: US 12,247,087 B2
(45) Date of Patent: Mar. 11, 2025

(54) BIOLOGICAL ACTIVE PEPTIDE FOR IMPROVING ENZYME ACTIVITY OF ACE2 AND APPLICATION THEREOF

(71) Applicants: ZHEJIANG QINGRONG BIOTECHNOLOGY DEVELOPMENT CO., LTD, Zhejiang (CN); YANGTZE DELTA REGION INSTITUTE OF TSINGHUA UNIVERSITY, ZHEJIANG, Zhejiang (CN)

(72) Inventors: Xiaojun Liu, Zhejiang (CN); Rongqing Zhang, Zhejiang (CN); Jing Zhang, Zhejiang (CN); Zehui Yin, Zhejiang (CN); Liping Yao, Zhejiang (CN); Zhen Zhang, Zhejiang (CN)

(73) Assignees: ZHEJIANG QINGRONG BIOTECHNOLOGY DEVELOPMENT CO., LTD, Zhejiang (CN); YANGTZE DELTA REGION INSTITUTE OF TSINGHUA UNIVERSITY, ZHEJIANG, Zhejiang (CN)

( * ) Notice: Subject to any disclaimer, the term of this patent is extended or adjusted under 35 U.S.C. 154(b) by 0 days.

(21) Appl. No.: 18/415,952

(22) Filed: Jan. 18, 2024

(65) Prior Publication Data

US 2024/0376150 A1 Nov. 14, 2024

Related U.S. Application Data

(63) Continuation of application No. PCT/CN2023/084817, filed on Mar. 29, 2023.

(30) Foreign Application Priority Data

Mar. 3, 2023 (CN) .......................... 202310196865.9

(51) Int. Cl.
  *C07K 7/08* (2006.01)
  *A61K 38/10* (2006.01)
  *A61P 31/14* (2006.01)

(52) U.S. Cl.
  CPC ................ *C07K 7/08* (2013.01); *A61K 38/10* (2013.01); *A61P 31/14* (2018.01)

(58) Field of Classification Search
  None
  See application file for complete search history.

(56) References Cited

FOREIGN PATENT DOCUMENTS

| | | |
|---|---|---|
| CN | 111346212 A | 6/2020 |
| CN | 114989250 A | 9/2022 |
| CN | 116023440 A | 4/2023 |
| JP | 2001106699 A | 4/2001 |
| WO | 2022029810 A1 | 2/2022 |

OTHER PUBLICATIONS

GenBank BAM76252.1 (SCO-spondin like, partial [Pinctada fucata], 2014) (Year: 2014).*
International Search Report of Corresponding Application No. PCT/CN2023/084817; Aug. 18, 2023; 5 Pgs.
Qi Yang, et al.; "Research progress in the pharmacological mechanism of angiotensin-converting enzyme 2 against SARS-COV-2"; Chin J. Hosp. Pharm.; vol. 40, No. 9; May 2020; 4 Pgs. with English Abstract.
SCO-spondin like, partial [Pinctada fucata]—Protein—NCBI; Date Accessed Jan. 10, 2024; 2 Pgs.
Pengru Liu; "Purification, Characterization and Evaluation of Inhibitory Mechanism of ACE Inhibitory Peptides from Pearl Oyster (*Pinctada fucata martensii*) Meat Protein Hydrolysate" Mar. drugs; (Aug. 8, 2019); 13 Pgs.

* cited by examiner

*Primary Examiner* — Sergio Coffa
(74) *Attorney, Agent, or Firm* — Cooper Legal Group, LLC

(57) ABSTRACT

The present application provides a biological active peptide from seawater pearl, the sequence of which is Ile-Pro-Ser-Thr-Thr-Pro-Phe-Pro-Ser-Thr-Thr-Val-Ala-Thr-Thr-Thr-Met, and the name of which is SCOL polypeptide. The biological active peptide can improve an ACE2 enzyme activity to 3.76 times, and can be applied in preparation of a drug improving an ACE2 activity, treating hypertension, anti-heart failure, anti-tissue fibrosis, anti-inflammation, and type 2 diabetes mellitus and the complication thereof, and relieving neuropathic pain. The biological active peptide can be specifically bound to the ACE2, effectively inhibits the 65% binding between novel coronavirus S protein and the ACE2, can be applied in preparation of an anti-coronavirus infection drug as an inhibitor, and specifically applied in preparation of anti-novel coronavirus drug.

2 Claims, 4 Drawing Sheets
Specification includes a Sequence Listing.

BIOLOGICAL ACTIVE PEPTIDE FOR IMPROVING ENZYME ACTIVITY OF ACE2 AND APPLICATION THEREOF

CROSS-REFERENCE TO RELATED APPLICATIONS

This application is a continuation of PCT application serial no. PCT/CN2023/084817, filed on Mar. 29, 2023, which claims the priority and benefit of Chinese patent application no. 202310196865.9, filed on Mar. 3, 2023. The entireties of PCT application serial no. PCT/CN2023/084817 and Chinese patent application no. 202310196865.9 are hereby incorporated by reference herein and made a part of this specification.

REFERENCE TO AN ELECTRONIC SEQUENCE LISTING

The contents of the electronic sequence listing (SequenceListing.xml; Size: 1,961 bytes; and Date of Creation: Jan. 17, 2024) is herein incorporated by reference.

TECHNICAL FIELD

The present application relates to a field of biological medicine, and in particular, to a pearl polypeptide derived from seawater pearl capable of improving enzyme activity of ACE2 and inhibiting a specific binding of a novel coronavirus S protein to the ACE2, and an application thereof.

BACKGROUND ART

Angiotensin-converting enzyme 2 (Angiotensin-converting enzyme 2, ACE2) is a type I of a transmembrane glycoprotein with a single extracellular catalytic structural domain. The ACE2 widely exists on various cell surfaces, such as those from heart, kidney, lung, cardiovascular system, intestines, testes, liver, pancreas, and central nervous system and the like. The ACE2 is a strongly negative regulatory factor in a renin-angiotensin system (renin-angiotensin system, RAS), and is an important therapeutic target for a relative disease caused by an unbalance of the RAS. The ACE2 can convert an angiotensin I into an angiotensin 1-9, so as to counteract the effect of ACE by reducing the level of a substrate lever; and convert an angiotensin II into an angiotensin 1-7, which, on the contrary, can induce a vasodilatation and reduce a blood pressure, acting as an effective vasodilator and an antiproliferative agent. Therefore, the ACE2 shows a protection function in the cardiovascular system and other organs.

The unbalance of the RAS system may result in vascular dysfunction, and the vascular dysfunction is a main reason of atherosclerosis and cardiovascular disease (CVD). A method for restoring the vascular dysfunction and other pathological changes is to counteract the effect of the angiotensin II by increasing the activity of the ACE2. Craceower et al find that the mice knocked out of ACE2 have a severe cardiac dysfunction, showing that the ACE2 may have a potential for restoring and regulating the heart function. Uri et al confirms that a reduction of the ACE2 activity is a selective biomarker of an abnormal cardiac contractile function. The lack of the ACE2 may increase the sensitivity for heart failure, and, it is further confirmed that, the activity of ACE2 is increased in a plasma of a patient with left ventricular systolic dysfunction. The left ventricular systolic dysfunction is an important risk factor of coronary heart disease, sudden death, heart failure and apoplexy. However, increasing the lever of the ACE2 can prevent and reverse the phenotype of the heart failure. The ACE2 and the angiotensin 1-7 have been a main protection approach for resisting the heart failure.

The unbalance of the RAS system is closely related to tissue fibrosis. RAS is currently recognized as one of endocrine system existing in local tissues such as heart, kidneys, lungs, and liver and so on, in which the angiotensin II is a main effector in the system, and mediates fibroblasts to promote tissue fibrosis via angiotensin receptor (ATR). As Konigshoff M et al found, the angiotensin II mediates the metastasis of the primary lung fibroblasts to promote lung fibrosis via AT1R receptor. In the kidney, it has been reported that a kidney injury is mostly mediated by the angiotensin II. The hypertensive renal disease is a common complication of the hypertensive, one of main mechanisms of which is an inflammation, an oxidative stress and a renal tissue fibrosis related to the Angiotensin II. There is a study reporting that the knockout of the ACE2 may cause the increased blood pressure, the glomerular injury and the renal fibrosis in diabetes mellitus mice.

In the heart, the unbalance of the RAS is involved in the myocardial fibrosis in the diabetes mellitus status, and PI3K/Akt/mTOR signaling pathway has an effect for regulating the myocardial fibrosis. The myocardial fibrosis caused by excessive proliferation, collagen synthesis increasement and the unbalanced proportion of the cardiac fibroblasts (CFs) is one of cellular pathological foundations of hypertension left ventricular hypertrophy. Therefore, the ACE2 becomes a target for multi tissue fibrosis treatment. The angiotensin 1-7 is not only involved in the blood pressure regulation, but also plays a role in the anti-tissue fibrosis. It has been reported that the expression lever of the serum ACE2 is negatively correlated to the degree of the liver fibrosis.

The unbalance of the RAS system plays a promoting role in the pathogenesis of some inflammatory diseases. Some studies found that the abnormal activation of the RAS system promotes the progression of vascular sclerosis disease, specific mechanism of which can include the inflammatory reaction promoted by the accumulation of the angiotensin II in the blood vessels for some reasons. There is some experimental evidences showing that the main inflammatory signaling pathways, such as NFκB pathway, can be activated by the reduced expression of the ACE2, which may cause a series of mechanisms promoting the vascular sclerosis, such as excessive release of inflammatory factors, dysfunction of endothelial cells, oxidative stress (a series of reaction causing the tissue injury), and thrombosis. In contrast, the activation of the signaling pathway related to the ACE2 and the metabolite thereof angiotensin 1-7 is considered to possess anti-inflammatory and anti-oxidation functions, and there is a study showing that the mechanism that the expression of the ACE2 is directly correlated to the activation of the anti-oxidant pathway Nrf2. There is a clinical evidence showing that the protein expression of the ACE2 is reduced in the formed atherosclerotic plaques, which certainly cause the accumulation of the angiotensin II, and reduces the generation of the angiotensin 1-7. Improving the activation of the ACE2 may play important anti-inflammatory and protection roles in the inflammation.

The ACE2 is an important target for treating type 2 diabetes mellitus and the complications thereof, the hypertension generally coexists with the insulin resistance, and the insulin resistance is a common pathophysiological foundation of the diabetes mellitus and the metabolic syndrome, and, therefore, improving the insulin resistance becomes one of important measures to prevent the diabetes mellitus and the metabolic syndrome. There is a study showing that endothelial dysfunction and inflammation induced by the angiotensin II and other factors play important roles in the development of the insulin resistance. Therefore, the influence of the overactive angiotensin II in the diabetes mellitus and the complications thereof can be eliminated by improving the expression or activity of the ACE2. The ACE2 can effectively delay the development of the insulin function decline in the diabetes mellitus patients by improving pancreatic blood flow perfusion, inhibiting cell apoptosis, promoting insulin secretion. In the pathophysiological process of microvascular and macrovascular lesions in the diabetes mellitus, the ACE2 exerts anti-ACE, and regulates the balance of heart, retina, kidney and blood vessel. The ACE2 and the activator thereof have extremely broad clinical application prospects in the prevention and treatment of the diabetes mellitus and the complications thereof.

Independent autocrine RAS system exists in the central nervous system, and the angiotensin II may participate in the transfer of the central nociceptive information as neurotransmitter or neuromodulator, which plays an important role in the generation of pain.

In recent years, there is a report showing that angiotensin receptor antagonists or other related peptides are applied in the treatment of clinical pain. Rice et al apply the small molecule AT2R antagonist EMA401 to 183 samples of the postherpetic neuralgia patients, which conducts the phase 2 clinical study of a double-blind, a randomized, and a placebo control. The result shows that EMA401 compared with the placebo possesses a good analgesic on the patients and possesses a well tolerance. The angiotensin 1-7 is an important neuromodulator of the regions related to arterial pressure reflex control, such as a hypothalamus and a ventrolateral medulla oblongata. In above position, the cardiovascular effects generated from the angiotensin 1-7 is blocked by the A-779 (MasR antagonists), which means that the angiotensin 1-7 can act on the brain Mas receptors. There is a study suggesting that the angiotensin 1-7 can act on the MasR and AT1R, wherein the anti-nociceptive generated by acting on the MasR is much greater than the pain response caused by acting on the AT1R. The existing study suggests that the angiotensin 1-7/Mas receptors may be an effective way to treat the neuropathic pain and the inflammatory pain. The neuropathic pain observed in the type 2 diabetes mellitus mice is related to the down regulation of ACE2/angiotensin 1-7/Mas receptors way, this down regulation is caused by the loss of the spinal dorsal horn neurons expressing ACE2. Since activating ACE2/angiotensin 1-7/Mas receptors way can alleviate the hyperalgesia, the best treatment strategy for alleviating the type 2 diabetes mellitus neuropathic pain. Therefore, improving the activity of ACE2 is an important target for developing drugs to alleviate neuropathic pain.

In summary, it has important disease treatment value that researching on how to amplify the enzymatic activity of the ACE2, such that more angiotensin II is converted into the angiotensin 1-7, thereby exerting beneficial biological effects.

A coronavirus S protein can be specifically bound to the ACE2 and mediates the process that the virus enters to the host cells, and such process is a start process that the coronavirus recognizes and invades into the host hells. The ACE2 is bound to the S protein in a way similar to the binding between the lock and the key, such that the virus is able to enter the human body. XU et al find that the S protein structure of the novel coronavirus is similar to the S protein structure of the SARS-coronavirus (SARS-COV) by biologically analysis, and the S protein and the ACE2 protein molecules on the surface host cells can act on each other, thereby infecting the host's epithelial cells. Therefore, the ACE2 molecules is key molecules in the infection of the novel coronavirus (2019-CoV-2), and is an essential protein for the novel coronavirus infecting the cells. Since the ACE2 plays an important role in the process of SARA-CoV-2 invading the host cells, it is an ideal preventing and treating strategy and has important meaning that the drugs blocking or delaying the function of the ACE2 as virus receptors can be developed.

SUMMARY

The present application provides a biological active peptide as a directly activator for ACE2, the active peptides can be used for preparation of a drug improving an activity of the ACE2, treating hypertension, anti-heart failure, anti-tissue fibrosis, anti-inflammatory, treatment of type 2 diabetes and complications thereof, and relieving of neuropathic pain. The active peptides can be specifically bound with the ACE2, thereby inhibiting the specific binding between a coronavirus S protein and the ACE2, which can be used for preparing a drug resisting the coronavirus infection as a blocker, and specifically for preparing a drug resisting the novel coronavirus.

A solution disclosed by the present application for realizing above purpose is:

A biological active peptide form seawater pearl binding and activating ACE2 naming as SCOL peptide, wherein an amino acid sequence is Ile-Pro-Ser-Thr-Thr-Pro-Phe-Pro-Ser-Thr-Thr-Val-Ala-Thr-Thr-Met (SEQ ID NO:1).

For Pinctada fucata pearl as an example, the biological active peptide isolated and purified from the Pinctada fucata pearl matrix protein, the preparing method thereof comprising following step:

(1) extracting pearl matrix protein: decalcifying the Pinctada fucata pearl powder by 1.5M ethylene diamine tetraacetic acid (EDTA), and freezing and drying to obtain a pearl matrix protein after the dialysis.

(2) enzymolyzing the pearl matrix protein: enzymolyzing the pearl matrix protein freeze dried power by a trypsin (trypsin), in which the enzymolysis time is 2 hours, centrifugating and collecting supernatant after inactivating in boiling water bath, performing a centrifugal and ultrafiltration by using the protein concentration centrifuge tube after filtering, in which the specification of the retention molecular weight is 3KD, collecting the filtrate with molecular weight less than 3KD, and freezing and drying to obtain an enzymolyzied pearl matrix protein polypeptide compound after concentrating.

(3) isolating and purifying a pearl matrix protein ACE inhibiting polypeptide: purifying the enzymolyzed pearl matrix protein polypeptide compound by using a high performance liquid chromatography, in which the chromatographic column is C18, the mobile phase A is a deionized water containing 0.1% trifluoroacetic acid, the mobile phase B is an acetonitrile containing 0.1% trifluoroacetic acid, the flow rate is 1 mL/min, and the UV detection wavelength is 280 nm, collecting samples with the retention time of 9.5 min, and freezing and drying to obtain an angiotensin converting enzyme 2 binding peptide after concentrating and the sequence thereof is Ile-Pro-Ser-Thr-Thr-Pro-Phe-Pro- Ser-Thr-Thr-Val-Ala-Thr-Thr-Thr-Met (SEQ ID NO:1), naming as a SCOL polypeptide.

The biological active peptide can be further prepared via an artificial synthesis based on the sequence disclosed in the present application.

The beneficial effect of the present application is:

(1) the biological active peptide according to present application is from pearl, the pearl is confirmed to be safe, no toxic, and edible, such that the active peptide possesses a good biological safety, a small molecular weight, and a high activity, is note only conducive to being isolated and purified, and is but also conducive to artificially synthetizing and preparing.

(2) the biological active peptide disclosed by the present application can improve an ACE2 enzyme activity to 3.76 times, and can be applied in treating related diseases caused by an unbalance of RAS system for preparing for drugs treating hypertension, anti-heart failure, anti-tissue fibrosis, anti-inflammation, and type 2 diabetes mellitus and the complication thereof, and relieving neuropathic pain.

(3) the biological active peptide disclosed by the present application can be specifically bound to the ACE2, effectively inhibits the 65% binding between the novel coronavirus S protein and the ACE2, can be applied in preparation of an anti-coronavirus infection drug as an inhibitor, and specifically applied in preparation of anti-novel coronavirus drug.

(4) the present application provides a reliable reference for further improving the technology and the medical development.

DETAILED DESCRIPTION

Figure 1:
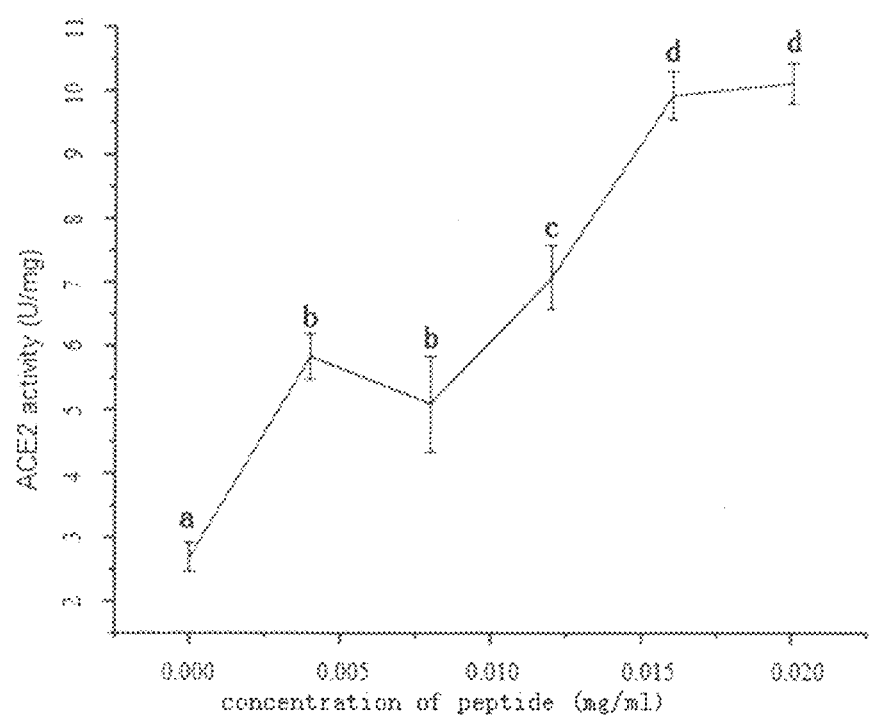
FIG. 1 is diagram of an activity influence of SCOL peptide in the present application (there is a significant difference between lowercase letters, p≤0.05)
Figure 2:
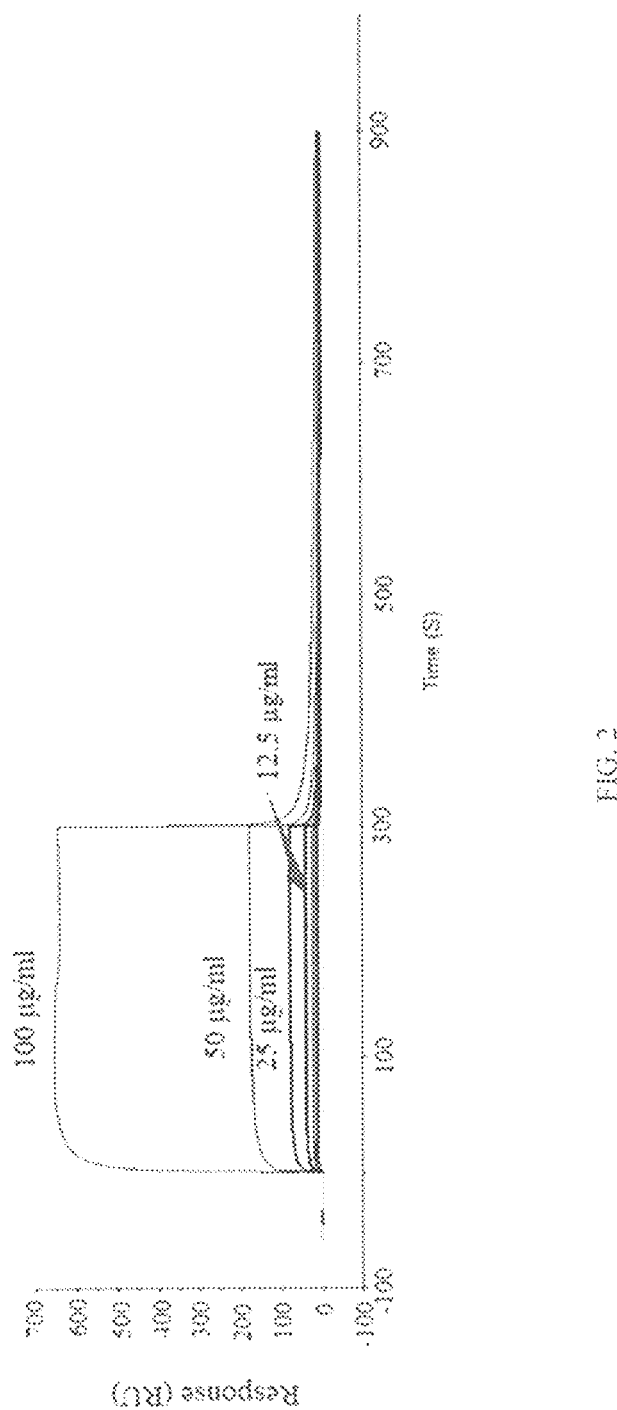
FIG. 2 is diagram of association and dissociation processes between the SCOL peptide and ACE2.
Figure 3:
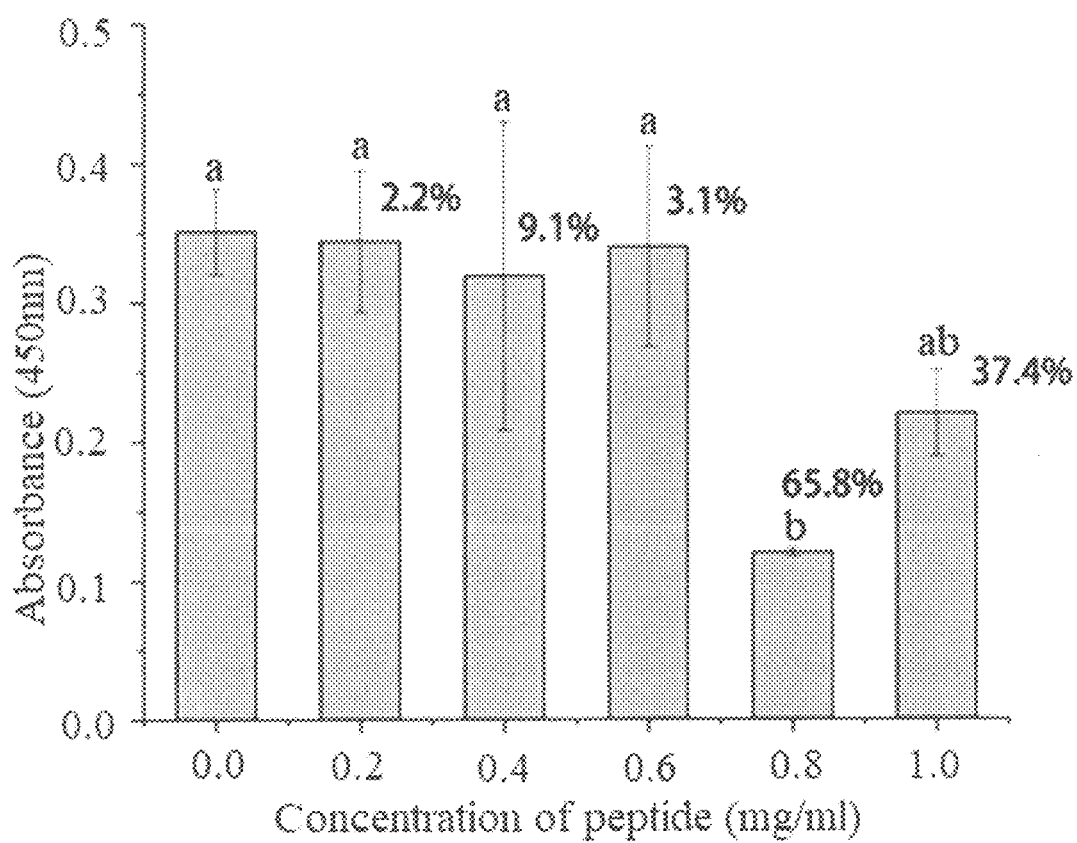
FIG. 3 is a diagram of a competitive association between the SCOL peptide and S protein for the ACE2 (there is a significant difference between lowercase letters, p≤0.05)
Figure 4:
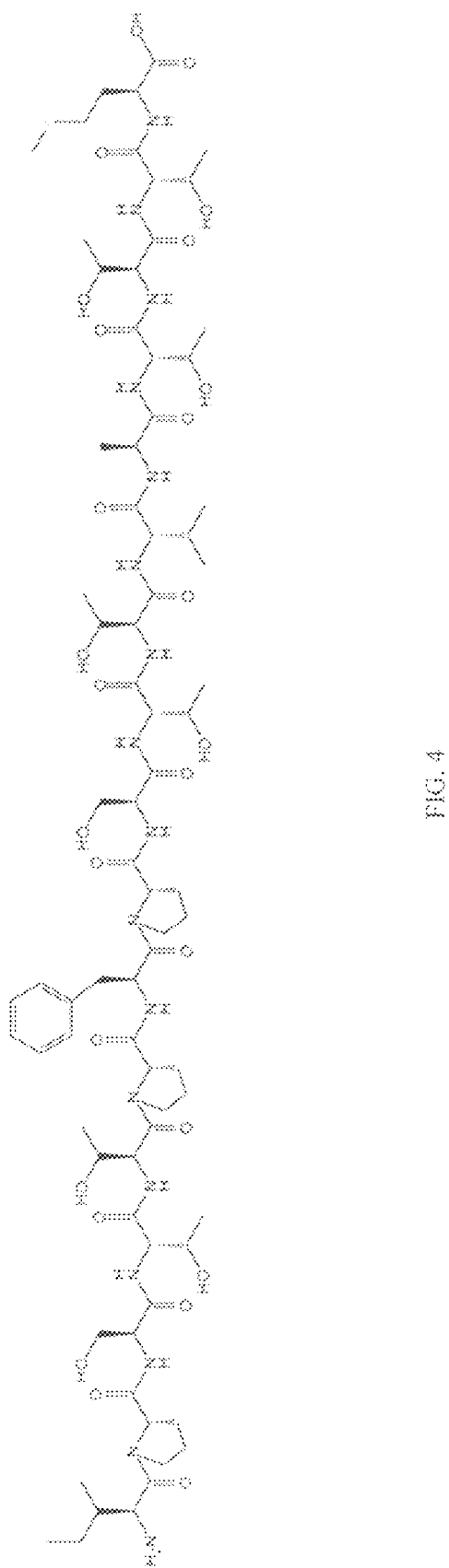
FIG. 4 is a molecular formula of the SCOL peptide in the present application.

The present application will be further described in detail below in combination with FIGS. 1-4 and examples.

Example 1: Preparation of SCOL Peptide (1) Extracting Pearl Matrix Protein

Pinctada fucata pipless pearl from Zhanjiang, Guangdong, was cleaned, dried, and fully crushed by using a traditional Chinese medicine grinding machine, during which the crushing was timely paused to cool a crushing container, thereby preventing damaging an active ingredient of the pearl due to overheating of the crushing container. A pearl powder was collected, placed in a beaker, added with 1.5 M EDTA with five times volume, placed in a 4° C. chromatography freezer, stirred for decalcification, loaded into a 50 mL high-speed centrifuge tube (10000 rpm), and centrifuged after 24 hours. Supernatant was collected, and filtered by using 0.2 μm microporous filter membrane to obtain a filtrate, which was placed in the 4° C. chromatography freezer and subjected to low temperature dialysis for 48 hours, during which water was replaced for multiple times. Freezing and drying were performed to obtain the pearl matrix protein.

(2) Enzymolyzing of the Pearl Matrix Protein

Freeze dried power of the pearl matrix protein was added with trypsin for enzymolysis. In particular, the activity of the trypsin was 10000 U/g, and the adding amount of the trypsin was 5% of the weight of the pearl matrix protein. The pH of the enzymolysis system was adjusted to 8.0, enzymolysis was performed in the thermostatic water bath at 50° C. for 2 hours. Then the mixture was inactivated in a boiling water bath, and centrifuged in a 50 mL high-speed centrifuge tube (10000 rpm). Supernatant was collected, filtered by using 0.2 μm microporous filter membrane to obtain a filtrate, which was subjected to a centrifuging ultrafiltration (4000 rpm by using the Millipore protein concentration centrifuge tube) to obtain a filtrate with molecular weight less than 3 KD, in which the retention specification of the built-in and low adsorption Ultracel PL ultrafiltration membrane is 3 KD. The filtrate was freeze dried to obtain an enzymolyzed pearl matrix protein polypeptide compound after concentrating.

(3) Isolating and Purifying of a Pearl Matrix Protein ACE Inhibiting Polypeptide The enzymolyzied pearl matrix protein polypeptide compound was purified by using a high performance liquid chromatography, in which the chromatographic column was C18 chromatographic column, the mobile phase A was a deionized water containing 0.1% trifluoroacetic acid, the mobile phase B was an acetonitrile containing 0.1% trifluoroacetic acid, the UV detection wavelength was 280 nm, and the flow rate was 1 mL/min. Samples with the retention time of 9.5 min was collected, and freeze dried to obtain an objective polypeptides after concentrating. In particular, the objective polypeptides named as SCOL polypeptide, and the sequence of which was Ile-Pro-Ser-Thr-Thr-Pro-Phe-Pro-Ser-Thr-Thr-Val-Ala-Thr-Thr-Thr-Met (SEQ ID NO:1).

Example 2: Detecting an Activity Influence of SCOL Polypeptide for ACE2

Detection was performed by using Biyuntian ACE2 active fluorescence detection kit; the principle was as follows. When ACE2 did not cut substrates, two fluorophores were close enough to each other, so that the fluorescence resonance energy transfer occurred, which led to no detection of fluorescence. When the substrate was fully cut by the ACE2, two ends of the polypeptide were separated, two fluorophores were separated, which led to detection of the fluorescence, such that the enzyme activity of the ACE2 protein enzyme can be sensitively detected by the fluorescence detection.

(1) preparation of samples: taking 50 mg mice liver tissue, adding 500 μL lysis solution to perform the homogenization treatment, centrifuging at 4° C. under 12000×g for 5 min, taking the supernatant for next step;

(2) setting standard curve: diluting the standard solution with buffer to concentrations of 0, 0.25, 0.5, 1, 2, 3, 4, 5 μM, individually adding 100 μL of which in each hole and repeating three times, and detecting to obtain the standard curve.

(3) adding 2 μL substrates in the 96 hole plate, individually adding 2.2 μL with concentration of 0.004, 0.008, 0.012, 0.016, 0.02 μg/μL of the total concentration in the PCR tubes, adding 8.8 μL supernatant sample in step (1), adding 96.8 μL buffer; and adding 11 μL lysis solution and 96.8 μL buffer in a blank control, mixing, sucking above 98 μL solution by a volley gun and adding to the 96 hole plate with substrates. Performing fluorescence detection by a fluorescence microplate reader after mixing, in particular, the setting temperature was at 37° C., the excitation wavelength was 325 nm, and the emission wavelength was 393 nm.

(4) Experimental Result

Calculating: the time interval of the sample group to be detected, in which the fluorescence intensity showed a linear relationship, was T, the variation of the fluorescence intensity in T was ΔRFU, which was substituted into the standard curve to obtain a generated amount A in the sample, in particular, the sample volume was V, the sample protein concentration was C, and the circulating formulation of the ACE2 protein enzyme activity was:

Ace2 Activity=A×V×T×C (U/Mg)

the experimental result was shown in FIG. 1, with the increase of the SCOL polypeptide concentration, the activity of the ACE2 in the samples showed an increasing trend, and, when the SCOL polypeptide concentration is 0.02 μg/μL, the highest ACE2 activity was 3.76 times for the initial activity.

Example 3: Detecting a Binding Ability Between SCOL Peptide and ACE2

The binding ability between the SCOL peptide and the ACE2 was detected by using Biacore X100, in particular, S serials SA chip (GE, lot: 20139043) was used, and buffer was 10×HBS-EP+ buffer. The ACE2 protein was fixed on the chip surface by a biotin-streptavidin way. The SCOL peptides with different concentration gradients was prepared, in particular, the concentrations individually were 3.125, 6.25, 12.5, 25, 25, 50, 100 μg/mL, the velocity of flow was 50 μL/min, the binding time was 300 s, the reaction temperature was 25° C., the dissociation flow rate was 30 μL/min, and the dissociation time was 600 s. The result was shown in FIG. 2, the detection curve of the SCOL peptides with the concentration of 100, 50, 25, 12.5, 6.25, 3.125 μg/mL were individually shown from top to down, which means that the SCOL peptides had a high affinity for the ACE2, in particular, the value of the dissociation constant $K_D$ (M) was $7.687 \times 10^{-5}$.

Example 4: Competitively Binding Analysis Between SCOL Peptide and S Protein for ACE2

Detection was performed by using RayBio®COVID-19 Spike-ACE2 Binding Assay Kit detection kit.

In particular, the principle is: the 96 hole plate of the kit was bound with the S protein recombinantly expressed, then the polypeptide was added to the hole when there was the ACE2 protein, and the small peptide could be bound to the key sites of the ACE2, thereby reducing the binding rate between the S protein and the ACE2 protein.

(1) Preparation of Mixture Between the SCOL Peptide and the ACE2 Protein

Diluting a 100×ACE2 protein concentrate in kit to a 10×ACE2 protein solution by a diluent, and diluting the concentration of the SCOL peptide to 0.2, 0.4, 0.6, 0.8, 1.0 mg/mL. In a PCR tube, adding the 110 μL SCOL peptides of each concentration, adding 11 μL 10×ACE2 protein diluent under the vortex mixing; and setting a control group without the SCOL peptide, in which the 100 μL diluent and the 11 μL 10×ACE2 protein diluent were mixed in the control group, each group had three replications.

(2) Detecting Binding Rate Between the ACE2 Protein and the S Protein by Enzyme-Linked Immunoassay S protein binding domain was coated on the bottom of the 96 hole plate. Sucking 100 μL solution of each group of PCR tubes from step (1) and adding to the 96 hole plate, sealing by using a microplate sealer, incubating overnight under gently shaking at 4° C.; discarding the solution and washing four times by using washing liquid, washing by adding 300 μl washing liquid to each hole; adding 100 μl prepared 1× detection antibody, which is a goat derived anti-ACE2 antibody that can bind to the S protein-ACE2 protein compound, to each hole, incubating under gently shaking 1 hour at room temperature, washing by using the washing liquid; adding 100 μl prepared 1×HRP binding antibody, which is a anti-"goat-IgG" labeled by HPR, incubating under gently shaking 1 hour at room temperature, washing by the washing liquid; adding 100 μl substrate chromogenic agent TMB to each hole, incubating under gently shaking 30 min without sunshine at room temperature; and adding a stop solution to stop the reaction, and detecting the absorbance under the wavelength at 450 nm, in which the absorbance was directly proportion to the amount of the S protein-ACE2 protein compound.

(3) Experimental Result

Referring to FIG. 3, when compared with the control group, the SCOL polypeptide group with each concentration all shown an inhibiting effect, in which the polypeptide group with 0.8 mg/mL concentrate had a highest inhibition rate reached to 65.8%, which means that the SCOL polypeptide had a strong binding ability with the ACE2, could competitively inhibit the binding between the novel coronavirus S protein and the ACE2, and had a good application prospect as a competitively inhibitor for S protein of the novel coronavirus.

Example 5: Sequence Analysis of SCOL Polypeptide

The SCOL polypeptide from the pearl matrix protein obtained from example 1 was detected by matrix-assisted laser desorption ionization time-of-flight/time-of-flight mass spectrometry (MALDI-TOF/TOF-MS), in which the molecular weight was 1794.8 Da, and the amino acid sequence was: Ile-Pro-Ser-Thr-Thr-Pro-Phe-Pro-Ser-Thr-Thr-Val-Ala-Thr-Thr-Thr-Met (as shown in SEQ ID NO:1).

The above are the preferred embodiments of the present application, which are not intended to limit the protection scope of the present application. Therefore, all equivalent changes made according to the structure, shape and principle of the present application should be covered within the protection scope of the present application.

What is claimed is:

1. A biological active peptide from seawater pearl consisting of SEQ ID NO: 1.

2. A drug comprising the biological active peptide according to claim 1, wherein the drug is any one selected from a group consisting of: an anti-coronavirus drug, a drug for improving angiotensin-converting enzyme 2 (ACE2) activity, a drug for treating hypertension, an anti-heart failure drug, an anti-tissue fibrosis drug, an anti-inflammation drug, a drug for treating type 2 diabetes mellitus and complications thereof, and a drug for relieving neuropathic pain.

* * * * *

```
                                SEQUENCE LISTING

Sequence total quantity: 1
SEQ ID NO: 1            moltype = AA   length = 17
FEATURE                 Location/Qualifiers
source                  1..17
                        mol_type = protein
                        organism = synthetic construct
SEQUENCE: 1
IPSTTPFPST TVATTTM                                                    17
```